United States Patent [19]

Kogure et al.

[11] Patent Number: 5,090,233

[45] Date of Patent: Feb. 25, 1992

[54] IN-LINE ANALYZER FOR PARTICLE SIZE DISTRIBUTION IN FLUE GAS

[75] Inventors: Nobuyuki Kogure, Toride; Masaaki Shirahase; Ikuo Tamori, both of Tsukuba, all of Japan

[73] Assignee: Japan as represented by Director General of Agency of Industrial Science and Technology, Tokyo, Japan

[21] Appl. No.: 662,576

[22] Filed: Mar. 1, 1991

[30] Foreign Application Priority Data

Jul. 4, 1990 [JP] Japan ............... 2-176648

[51] Int. Cl.$^5$ ........................... G01N 15/02
[52] U.S. Cl. ................. 73/28.05; 73/863.22; 73/865.5
[58] Field of Search ........... 73/28.05, 863.22, 865.5, 73/28.06

[56] References Cited

U.S. PATENT DOCUMENTS 4,590,792  5/1986  Chiang .................. 73/28.06
4,640,140  2/1987  Burghoffer et al. ......... 73/863.22

FOREIGN PATENT DOCUMENTS 595658  3/1978  U.S.S.R. ................ 73/863.22
1052939  11/1983  U.S.S.R. ................ 73/28.05

*Primary Examiner*—Hezron E. Williams
*Assistant Examiner*—Joseph W. Roskos
*Attorney, Agent, or Firm*—Wenderoth, Lind & Ponack

[57] ABSTRACT

A particle-size distribution analyzer in a vent gas or flue gas which can be in a gas carrying line of a dust- and/or mist-producing process is provided. The analyzer comprises: a series of particle-size classifying units each consisting of a gas-ejection nozzle of an opening having a diameter different from the others and an impaction plate mounted on a revolvable turret in such a fashion that the series of the units can communicate with a suction nozzle in the gas flow line one by one successively in a decreasing order of the nozzle opening diameter; and a light-scattering particle-concentration detecting system which gives the concentration data after particle-size classification as a function of the cut-off size of the particles contained in the gas. In another embodiment, a heater to evaporate the liquid constituent in the mist particles and a second concentration-detecting system are provided downstream of the first concentration-detecting system so that measurements of the particle size distribution can be conducted for the dust particles and mist particles separately.

2 Claims, 2 Drawing Sheets

IN-LINE ANALYZER FOR PARTICLE SIZE DISTRIBUTION IN FLUE GAS

BACKGROUND OF THE INVENTION

The present invention relates to an in-line analyzer for particle size distribution in a particulate-containing flue gas or vent gas or, more particularly, to an in-line analyzer for particle size distribution in a flue gas or vent gas containing dusty and/or misty particles separately for the solid and liquid constituents.

Needless to say, any flue gases from a combustion furnace and vent gases in the gas-carrying duct from a powder-processing plant, for example, contain a considerable amount of dust, which may be soot formed by combustion of fuels or scattered powder. In addition to the dust particles, i.e. solid particles suspended in the gas, these gases sometimes contain mist which means extremely fine liquid particles or droplets suspended in the gas. Further, various chemical plants utilize a process of gas scrubbing with an aqueous alkaline solution or by spraying of brine resulting in the solid constituent such as the alkali or salt dissolved in the mist particles of the vent gas from the process. Such a dust-and/or mist-containing gas is generally called aerosol.

Various instruments working on several principles are known for the determination of the concentration and size distribution of particulates in aerosol. However, a so-called cascade impactor is the only class of such instruments by which size distribution of dust particles in a vent gas can be determined in field work as is the case in the cascade impactors developed and reported by A. A. Anderson, et al. in Journal of Bacteriology, volume 76, pages 471–484 (1958), by V. A. Marple, et al. in Journal of Aerosol Science, volume 7, pages 425–433 (1976) and by M. J. Pilat, et al. in Journal of Atmospheric Environment, volume 4, pages 671–679 (1970). The essential structure of the instrument of this type includes several particle-size classifying units in a cascade arrangement of which each unit consists of a tapered gas-ejection nozzle and an impaction disc positioned just below the gas-ejection nozzle to face the nozzle opening, the opening of a nozzle positioned higher having a larger diameter than that positioned lower. When a dust-containing gas is ejected out of the uppermost nozzle with a specified velocity at the impaction disc, the gas flow is deflected by the impaction disc while the dust particles having a diameter exceeding a certain limit or so-called cut-off size break away out of the gas flow to impinge at the impaction disc and are captured thereon due to the inertial force of the particles in proportion to the square of the particle diameter and the velocity. The gas flow freed from the dust particles of the fraction in the coarsest range of diameters is then ejected out of the second nozzle and accelerated to have a larger velocity to impinge at the second impaction disc, and so on. In this manner, each of the impaction discs captures dust particles contained in the vent gas feed, the dust particle diameters being larger on the impaction disc at a higher position than on a disc at a lower position. Therefore, the particle size distribution or the amounts of the particles in the respective fractions can be determined by demounting the impaction discs and accurately weighing each of them to determine the amount of the dust particles deposited thereon.

In an actual procedure for the measurement of dust particles according to the above described principle, an instrument containing several units each composed of a gas-ejection nozzle and an impaction disc is inserted into the flue or gas duct and the dust-containing gas is drawn therethrough at the same velocity as the flow of the flue gas by suction with a suction nozzle for a length of time and then the impaction discs having the dust particles deposited thereon and demounted from the instrument are brought to a laboratory where each of the discs is weighed to determine the amount of the respective fraction of the particles having diameters in a certain range before final calculation of the particle size distribution and concentration in the flue gas.

The cascade impactor described above is not an instrument suitable for daily or routine work in respect of the large amount of labor and time taken to obtain the final results of determination. As is understood from the principle of the method, in addition, the instrument is not suitable for the in-line measurement to speedily follow the variation of the particle size distribution and concentration of dust particles contained in a flue gas in the lapse of time. When the gas contains mist particles as in the exhaust gas at the outlet of a flue-gas desulfurization plant, moreover, the mist particles deposited on the impaction disc form a liquid layer which eventually overflows out of the disc so that no accurate determination can be performed with such a conventional cascade impactor.

SUMMARY OF THE INVENTION

The present invention accordingly has an object to provide a novel instrument free from the above mentioned disadvantages of the prior art instruments for the determination of the particle size distribution in aerosols containing not only dust particles but also mist particles and suitable for daily use as being built in a process line of gas flow.

Another object of the invention is to provide an instrument for the determination of the particle size distribution in aerosol by which the amount of the dust particles and mist particles can be determined separately.

A further object of the invention is to provide an instrument for the determination of the particle size distribution in aerosol containing mist particles by which, when a solid material is contained dissolved as a solute in the mist droplets, the particle size distribution relative to the solid material alone can be determined.

Thus, the in line particle size analyzer of the present invention for a dust- and/or mist-containing gas comprises, in an embodiment:

(a) a gas flow line having a suction nozzle;

(b) a revolvable turret built in the gas flow line mounting a plurality of particle size classifying units, each unit consisting of a gas-ejection nozzle and an impaction plate positioned to face the gas-ejecting opening of the gas-ejection nozzle keeping a distance, arranged at equal distances from the axis of the revolvable turret in such a fashion that, when the revolvable turret is revolved, the gas-inlet opening of each of the gas ejection nozzles is successively communicated with the outlet of the suction nozzle of the gas flow line, the gas-ejection opening of each of the gas-ejection nozzles having a different diameter from the others; and (c) a light scattering particle-concentration sensor unit built downstream of the revolvable turret as the component (b) in the gas flow line comprising a light projector to project light to the gas flowing in the gas flow line and a light detector to detect the light from the light projector after being scattered by the particles contained in the flowing gas.

The in-line particle size analyzer of the present invention for a dust- and/or mist-containing gas in another embodiment comprises, in addition to the above described components (a), (b) and (c):

(d) a means for heating the gas flowing in the gas flow line positioned downstream of the component (c) to evaporate the liquid constituent in the particles; and (e) a second light-scattering particle-concentration sensor unit built downstream of the heating means as the component (d) in the gas flow line comprising a second light projector to project light to the gas flowing in the gas flow line and a second light detector to detect the light from the second light projector after being scattered by the particles contained in the flowing gas.

DETAILED DESCRIPTION OF THE PREFERRED EMBODIMENTS

As is described above, the most characteristic feature of the inventive particle size analyzer for a dust- and/or mist-containing gas consists in the combined use of a series of particle-size classifying units mounted on a revolvable turret and a light-scattering particle-concentration sensor unit positioned in the gas flow line downstream of the particle-size classifying units, although the structure of a single particle-size classifying unit is known from the disclosure in, for example, Japanese Patent Kokai 59-151036 and 60-15542 relative to a cascade impactor and the principle of the light-scattering particle-concentration sensor unit is known from the disclosure in, for example, Japanese Patent Kokai 56-76032 and Japanese Patent Publication 59-25968. By virtue of this unique feature, the inventive particle size analyzer can be built in a flow line of a dust- and/or mist-containing gas and provides a means to continuously monitor and give information on the particle size distribution in the gas coming out of any dust- and/or mist-producing process.

In the following, the inventive particle size analyzer for a dust- and/or mist-containing gas is described in more detail with reference to the accompanying drawing.

Figure 1:
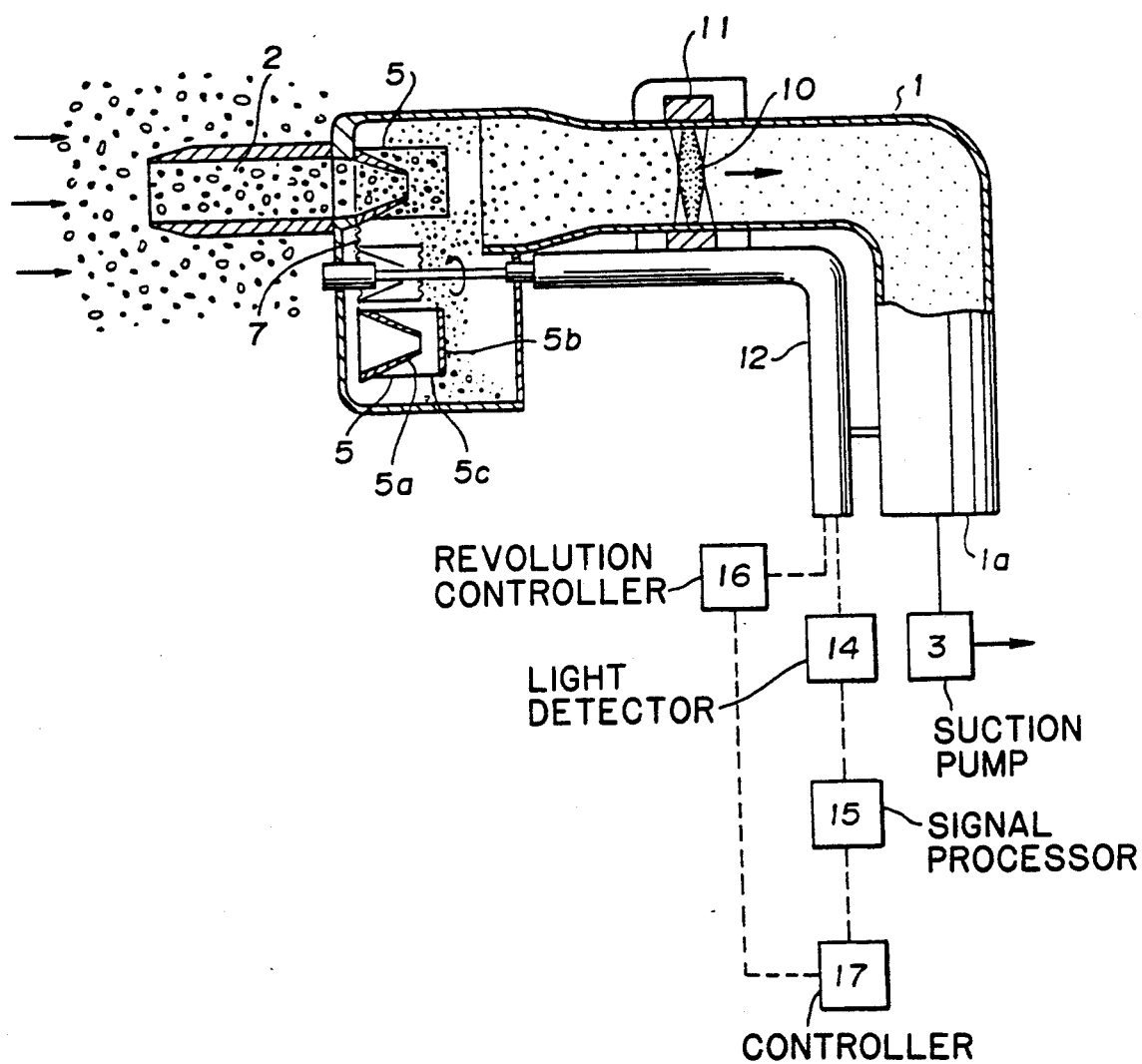
FIG. 1 is a schematic cross sectional view of the inventive particle size analyzer having a single light-scattering particle-concentration sensor unit.

FIG. 1 is a schematic cross sectional view of the inventive particle size analyzer built in a gas carrying duct such as a flue. The flowing aerosol (shown by the arrows at the left end) is introduced into the suction nozzle (2) in the gas flow line (1) at a constant velocity from the left-end opening and discharged out of the right-end opening (1a) by suction with a suction pump (3) connected at the end of the gas flow line (1) to enter one of the particle-size classifying units ($5_1$, $5_2$, $5_3$, ..., $5_n$) at the gas-receiving opening, each unit consisting of a tapered or funnel-like gas-ejection nozzle (5a) and an impaction plate (5b) facing the ejection opening of the nozzle (5a) keeping a distance as being supported by the supporting stems (5c), which nozzle (5) is just in communication with the exit of the suction nozzle (2) by means of revolving of the revolvable turret (7) mounting the particle-size classifying units ($5_1$ to $5_n$) at equal distances from the axis of the turret (7). When the particle-containing gas is ejected out of the gas-ejection opening of the nozzle (5a) to the impaction plate (5b), the gas flow is deflected by the impaction plate (5b) while the particles contained in the gas flow having larger diameters than a cutoff size determined by the diameter of the gas-ejection opening of the nozzle (5a) are not carried by the deflected gas flow but impinge at the impaction plate (5b) where they are captured to break away from the gas flow. Therefore, the gas flow deflected at the impaction plate (5b) to go ahead downstream contains smaller particles than the cut-off size only to be determined by the light-scattering particle-concentration sensor unit (11). A series of such particle-size classifying units ($5_1$ to $5_n$) are mounted on the revolvable turret (7) at equal distances from the revolving axis of the revolvable turret (7) in such a fashion that, when the revolvable turret (7) is revolved around the axis, the plurality of the particle-size classifying units ($5_1$ to $5_n$) are successively communicated one by one with the exit end of the suction nozzle (2). The gas-ejection opening of each of the gas-ejection nozzles (5a) has a diameter different from those of the other nozzles. It is convenient, though not limitative, that the particle-size classifying units ($5_1$ to $5_n$) are mounted and arranged around the revolving axis of the revolvable turret (7) in a decreasing or increasing order of the diameters of the respective gas-ejection openings of the nozzles (5a) so that the light-scattering particle-concentration sensor unit (11) may produce signals corresponding to the particle concentrations in the flowing gas after the particle-size classification in the decreasing order of the cut-off size. Besides a series of the particle-size classifier units ($5_1$ to $5_n$), the revolvable turret (7) should have a free-flow passage opening for the gas without the particle-size classifier unit, through which the particle-containing gas can be passed and transferred to the light-scattering particle-concentration sensor unit (11) without the effect of particle-size classification.

The gas coming out of one of the particle-size classifier units ($5_1$ to $5_n$) is then transferred into the concentration-detecting zone (10) between the light-projecting and light-receiving windows of the particle-concentration detecting sensor unit (11) at the terminal of an optical-fiber cable protected by a protecting tube (12) and leading to a light source and light detector (14). The signal generated in the light detector (14) is converted in the signal processor (15) into the concentration of the particles in the gas flowing through the concentration-detecting zone (10) and the data is stored in the memory of the controller (17) which thereupon generates a signal to drive the revolution controller (16) so as to revolve the revolvable turret (7) by one step bringing the next-positioned particle-size classifier unit (5) into communication with the exit end of the suction nozzle (2) in the gas flow line (1).

When the particle-containing gas transferred into the concentration-detecting zone (10) is after flowing through the free-flow passage opening in the revolvable turret (7), the data of concentration $C_0$ stored in the controller (17) represents the total concentration of the particles in the flowing gas. Beginning with the free-flow passage opening, revolution of the revolvable turret (7) brings the particle-size classifier units ($5_1$ to $5_n$) successively in a decreasing order of the cut-off sizes $d_1$, $d_2$, $d_3$, $d_4$, ..., $d_n$ so that the concentration data $C_1$, $C_2$, $C_3, C_4, \ldots, C_n$ stored in the memory of the controller (17) represent the concentrations of the particles in the respective gas flows having smaller particle sizes than $d_1, d_2, d_3, d_4, \ldots d_n$, respectively. After completion of one revolution of the revolvable turret (7) in this manner, the data stored in the memory of the controller (17) including $C_0, C_1, C_2, C_3, C_4, \ldots C_n$ are processed in the signal processor (15) to be converted into desired information, for example, relative to the cumulative particle size distribution, contents of the particle fractions having particle sizes in particular ranges and the like in the concentration.

Figure 2:
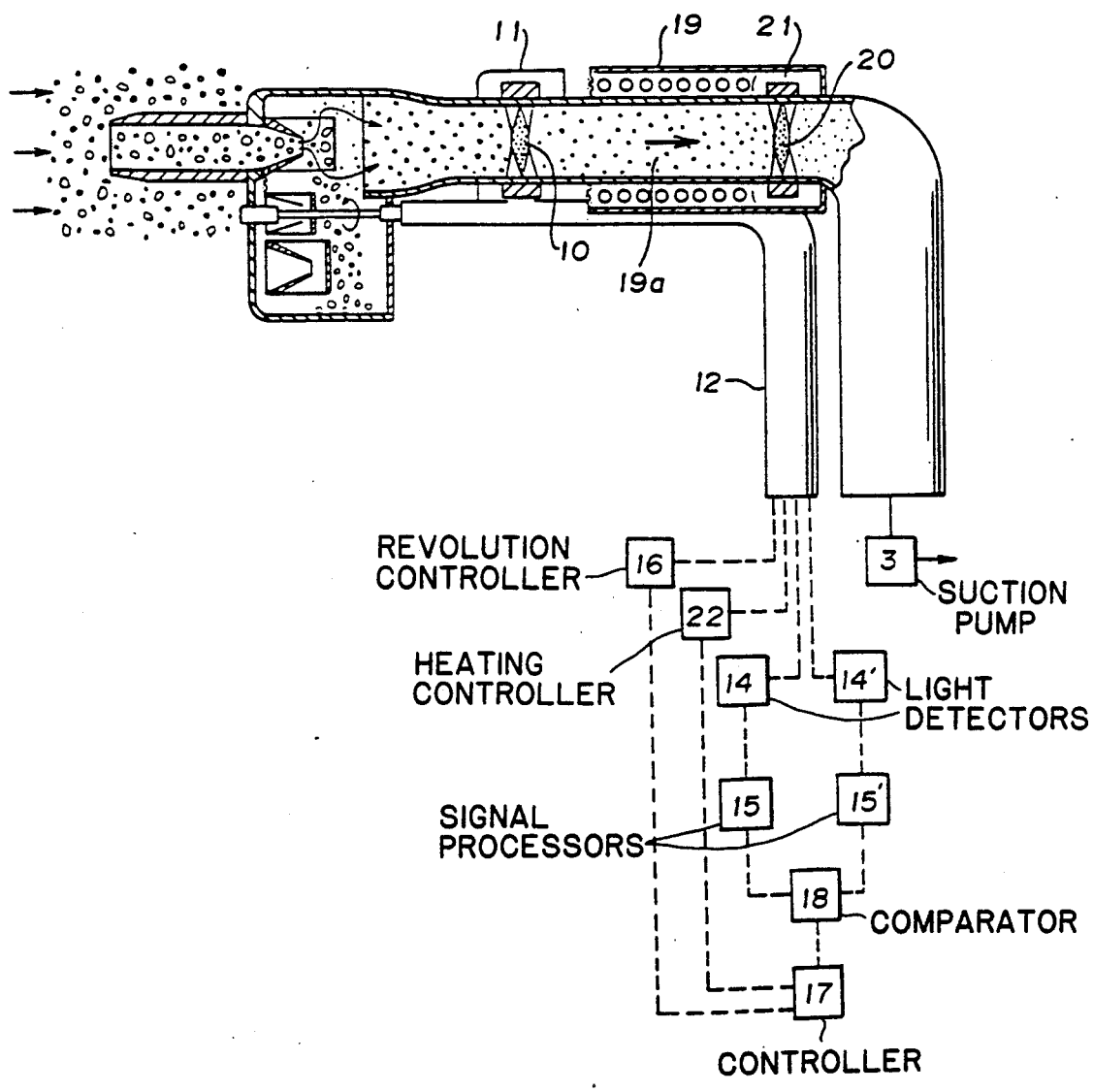
FIG. 2 is a schematic cross sectional view of the inventive particle size analyzer having two light-scattering particle concentration sensor units with a heating means therebetween.

FIG. 2 in the accompanying drawing illustrates another embodiment of the inventive particle size analyzer by a schematic cross sectional view. In this embodiment, a heating means (19), for example, having an electric heater is provided downstream of the light scattering particle-concentration sensor unit (11) in the embodiment illustrated in FIG. 1 to surround the gas flow line (1) and a second light-scattering particle-concentration sensor unit (21) is provided downstream of the heating means (19). The principle and constitution of the second concentration-detecting system including this second light-scattering particle-concentration sensor unit (21) are substantially the same as in the first concentration-detecting system described above including another set of a light projector and a light detector to detect the concentration of the particles contained in the gas flow in the second concentration-detecting zone (20) which is in direct downstream of the heating means (19).

When the gas flow coming from the first concentration detecting zone (10) contains both dust particles, i.e. solid particles, and mist particles, i.e. liquid particles, and the heating means (19) is in operation to heat the gas in the evaporation zone (19a) at a sufficiently high temperature, the mist particles are evaporated there so that the gas flow entering the second concentration detecting zone (20) contains the dust particles only. The signals generated in the second light detector (14') by the dust particles only are processed in the second signal processor (15') and stored in the controller (17), which also drives the heating controller (22), through a comparator (18). Thus, the data stored in the controller (17) include the concentration data $C_0', C_1', C_2', \ldots, C_n'$ obtained in the second concentration detecting system by the one revolution of the revolvable turret (7) corresponding to the concentration data $C_0, C_1, C_2, \ldots, C_n$ obtained in the first concentration detecting system, respectively, of which the data set of $C_0$ to $C_n$ represents the total concentrations of the dust and mist particles while the data set of $C_0'$ to $C_n'$ represents the concentrations of the dust particles only. Therefore, sets of useful information of the particle size distribution can be determined continuously and separately for the dust particles and mist particles in the gas.

The particle size analyzer having two concentration-detecting systems as illustrated in FIG. 2 is also useful when mist particles contain a solid material dissolved in the liquid droplets as in a gas coming from a gas scrubber using an aqueous alkaline solution as the scrubbing liquid or a vent gas coming from a desulfurization plant. Namely, the first concentration-detecting system serves for the determination of the particle size distribution of the mist particles as a whole while the second concentration-detecting system serves for the determination of the solute concentration in the gas after evaporation of the liquid constituents in the evaporation zone (19a). Thus, continuous information can be obtained on the particle size distribution of the mist particles along with the solute concentration therein contributing to the solution of the problems relative to air pollution due to the solute-containing mist particles carried by a vent gas.

What is claimed is:

1. An in-line particle size analyzer for a gas containing dust particles, mist particles or a combination thereof which comprises:

(a) a gas flow line having a suction nozzle;

(b) a revolvable turret built in the flow line of the gas mounting a plurality of particle size classifying units, each unit consisting of a gas-ejection nozzle and an impaction plate positioned to face the gas-ejecting opening of the gas-ejection nozzle keeping a distance, arranged at equal distances from the revolving axis of the revolvable turret in such a fashion that, when the revolvable turret is revolved, the gas inlet opening of each of the gas-ejection nozzles is successively communicated with the outlet of the suction nozzle of the gas flow line, the gas-ejection opening of each of the gas-ejection nozzles having a different diameter from the others; and (c) a light-scattering particle-concentration sensor unit downstream of the revolvable turret, in the gas flow line comprising a light projector to project light to the gas flowing in the gas flow line and a light detector to detect the light from the light projector after being scattered by the particles contained in the flowing gas.

2. The in-line particle size analyzer for a gas containing dust particles, mist particles or a combination thereof as claimed in claim 1 which further comprises:

(d) a means for heating the gas flowing in the gas flow line positioned in the gas flow line downstream of the light-scattering particle-concentration sensor unit to evaporate the liquid constituent in the particles; and (e) a second light-scattering particle-concentration sensor unit built downstream of the heating means in the gas flow line comprising a second light projector to project light to the gas flowing in the gas flow line and a second light detector to detect the light from the second light projector after being scattered by the particles contained in the flowing gas.

* * * * *